United States Patent
Kroll et al.

(10) Patent No.: US 7,305,270 B1
(45) Date of Patent: Dec. 4, 2007

(54) CARDIAC PACING/SENSING LEAD PROVIDING FAR-FIELD SIGNAL REJECTION

(75) Inventors: Mark W. Kroll, Crystal Bay, MN (US); John R. Helland, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 157 days.

(21) Appl. No.: 11/112,508

(22) Filed: Apr. 21, 2005

(51) Int. Cl.
*A61N 1/05* (2006.01)

(52) U.S. Cl. ............... 607/127; 607/119; 607/122; 607/126; 600/374; 600/375

(58) Field of Classification Search ............ 607/9, 607/115, 116, 119, 122, 123, 126–132; 600/372, 600/374, 375, 393, 509, 521
See application file for complete search history.

(56) References Cited

U.S. PATENT DOCUMENTS

| | | | |
|---|---|---|---|
| 3,977,411 A | 8/1976 | Hughes, Jr. et al. | 128/419 P |
| 4,140,132 A | 2/1979 | Dahl | 128/419 PG |
| 4,579,119 A | 4/1986 | Callaghan | 128/419 PG |
| 4,600,017 A | 7/1986 | Schroeppel | 128/784 |
| 4,892,102 A * | 1/1990 | Astrinsky | 600/374 |
| 4,991,583 A * | 2/1991 | Silvian | 607/13 |
| 5,324,327 A | 6/1994 | Cohen | 607/122 |
| 5,325,870 A * | 7/1994 | Kroll et al. | 607/122 |
| 5,336,253 A | 8/1994 | Gordon et al. | 607/122 |
| 5,342,414 A | 8/1994 | Mehra | 607/127 |
| 5,431,681 A | 7/1995 | Helland | 607/4 |
| 5,545,201 A | 8/1996 | Helland et al. | 607/127 |
| 5,571,163 A | 11/1996 | Helland | 607/123 |
| 5,899,929 A | 5/1999 | Thompson et al. | 607/28 |
| 5,968,086 A | 10/1999 | Bonner et al. | 607/122 |
| 6,418,348 B1 * | 7/2002 | Witte | 607/122 |
| 6,687,550 B1 | 2/2004 | Doan | 607/127 |
| 6,704,605 B2 | 3/2004 | Soltis et al. | 607/127 |
| 2002/0103523 A1 * | 8/2002 | Helland et al. | 607/122 |
| 2002/0123784 A1 * | 9/2002 | Westendorp | 607/122 |
| 2003/0220676 A1 * | 11/2003 | Helland | 607/122 |
| 2006/0122679 A1 * | 6/2006 | Wengreen et al. | 607/122 |

FOREIGN PATENT DOCUMENTS

| | | |
|---|---|---|
| EP | 0824935 A2 | 2/1998 |
| EP | 0824935 A3 | 12/1999 |
| EP | 0632992 B1 | 5/2000 |
| EP | 0673269 B1 | 3/2001 |
| WO | WO 99/43381 | 9/1999 |

* cited by examiner

*Primary Examiner*—Kristen D. Mullen
*Assistant Examiner*—Eugene T Wu

(57) ABSTRACT

A proximal end of a lead body carries a connector assembly. A first electrical conductor within the lead body electrically connects a tip electrode to a first electrical contact on the connector assembly. A collar electrode is carried by a distal end portion of the lead body. A second electrical conductor within the lead body electrically connects the collar electrode to a second electrical contact on the connector assembly. A ring electrode, carried by the distal end portion of the lead body, is disposed proximally of the collar electrode in spaced-apart relationship thereto and is connected through a switching device to a node point along the first conductor. The switching device has a first state permitting an electrical current to be conducted between the ring electrode and the node point and a second state in which the ring electrode is electrically isolated from the node point. Preferably, the switching device comprises a diode.

13 Claims, 6 Drawing Sheets

CARDIAC PACING/SENSING LEAD PROVIDING FAR-FIELD SIGNAL REJECTION

FIELD OF THE INVENTION

The present invention relates generally to cardiac pacing and sensing, and particularly to an implantable, transvenous, far-field signal-rejecting, bipolar cardiac pacing and sensing lead and to a system incorporating such a lead.

BACKGROUND OF THE INVENTION

Cardiac pacemaker lead systems fulfill two functions. The first function is to provide an electrical conduit by which a pacemaker output pulse is delivered to stimulate the local tissue adjacent to the distal tip of the lead. The second function is to sense local, intrinsic cardiac electrical activity that takes place adjacent to the distal tip of the lead.

The advantages of providing pacing therapies to both the right and left heart chambers are well established. For example, in four chamber pacing systems, four pacing leads, typically bipolar leads, are positioned for both pacing and sensing of the respective heart chambers. To provide right side pacing and sensing, leads are implanted directly in the right atrium and/or right ventricle. To provide left side stimulation and sensing, leads are transvenously implanted in the coronary sinus region, for example, in a vein such as the great vein, the left posterior ventricular (LPV) vein, or other coronary veins, proximate the left ventricle of the heart. Such placement avoids the risks associated with implanting a lead directly within the left ventricle which can increase the potential for the formation of blood clots which may become dislodged and then carried to the brain where even a small embolism could cause a stroke.

One of the problems with cardiac pacing and sensing systems is their inability to suppress far-field electrical signals. These signals are generated by depolarizations of body tissue in areas remote from the local sensing site and are manifested as propagated voltage potential wavefronts carried to and incident upon the local sensing site. A far-field signal may comprise the intrinsic signal originating from the chamber of the heart opposite the one in which a lead electrode is located. For example, for a lead electrode implanted in the right atrium, the ventricular R-wave comprises a far-field signal whose amplitude can easily swamp the smaller P-wave signal sought to be sensed thereby making difficult the discrimination of a P-wave from the higher energy QRS complex (sometimes referred to as the R-wave).

The sensing electrode(s) detect(s) the voltages of these far-field signals and interpret them as depolarization events taking place in the local tissue when such polarizations are above the threshold sensing voltage of the system. When far-field signal voltages greater than the threshold voltage are applied to the sensed signal processing circuitry of the pulse generator or pacemaker, activation of certain pacing schemes or therapies can be erroneously triggered.

With the development of programmable, universal stimulation/sensing systems, that is, three- and four-chamber combination pacemaker-cardioverter-defibrillators, accurate sensing of cardiac signals has become even more critical, and the management, suppression and/or elimination of far-field signals is vitally important to allow appropriate device algorithms to function without being confused by the undesirable far-field signals.

U.S. Pat. No. 4,579,119 discloses a tripolar atrial pacing and sensing lead comprising a passive tip electrode and a pair of spaced-apart ring electrodes. The distal ring electrode, that is, the ring electrode positioned intermediate the tip electrode and the more proximal of the pair of ring electrodes, is at all times connected to one of the two input terminals of a sense amplifier. A multiplexer at the proximal end of the lead selectively connects the remaining electrodes to a pulse generator and to the sense amplifier. Thus, during pacing the tip electrode and the proximal ring electrode are connected to the pulse generator. During sensing, the multiplexer connects the parallel combination of the tip electrode and the proximal ring electrode to the other sense amplifier input. The placement of this tripolar lead in the right atrium is said to reduce both cross-sensing, that is, the sensing of far-field signals originating in the ventricle as well as polarization potentials which would otherwise mask the evoked response. The '119 patent requires an electrical conductor extending the entire length of the lead body for each of the electrodes and does not deal with active fixation leads, that is, those incorporating an extendable/retractable helical screw-in fixation element.

U.S. Patent Application Publication US2002/0123784A1 discloses a tripolar pacing and sensing lead including three electrodes separated by interelectrode spacings that are said to maximize both sensing and pacing activities. The electrode pair comprising a passive tip electrode and a first ring electrode provides local sensing capabilities within either the atrium or the ventricle, while the electrode pair comprising the tip electrode and a second ring electrode provides pacing capabilities. Far-field artifacts are indicated to be virtually eliminated by minimizing the distance between the two sensing electrodes to provide a tightly spaced dipole that will detect the wave front passing the electrodes without susceptibility to far-field signals. Like U.S. Pat. No. 4,579,119, the tripolar electrode arrangement of publication US2002/0123784A1 requires a separate electrical conductor running the length of the lead for each electrode and is not directed to active fixation leads.

It is also recognized that in bipolar pacing and sensing leads comprising a fixed collar electrode at the tip of the lead and a fixation element in the form of a helical screw electrode extendable and retractable relative to the lead tip, the distance between the collar electrode and the electrically active portion of the helical screw electrode should be minimized to suppress responsiveness to far-field signals. See, for example, U.S. Pat. No. 5,545,201, which is herein incorporated by reference, disclosing a partially uninsulated, electrically active helical fixation element paired with a collar electrode to provide a closely spaced dipole. Because of the development of necrotic tissue about the helical fixation element and the resulting higher pacing thresholds, a ring electrode disposed proximally of the collar electrode is often included to ensure capture. However, the added ring electrode has required an additional electrical conductor within the lead body, tending to undesirably increase the diameter of the lead.

SUMMARY

In accordance with one, specific, exemplary embodiment, there is provided a bipolar cardiac lead for transmitting electrical pacing and sensing signals between an electrical medical device and selected cardiac tissue along two electrical conductors. The lead comprises a lead body having a proximal end, a distal tip and a distal end portion extending proximally from the distal tip. The proximal end of the lead body carries a connector assembly electrically connectable to the electrical medical device. The lead body further carries a tip electrode at the distal tip of the lead body, a first electrical conductor within the lead body electrically connecting the tip electrode to a first electrical contact on the connector assembly. A second electrode is carried by the distal end portion of the lead body at the distal tip thereof. A second electrical conductor within the lead body electrically connects the second electrode to a second electrical contact on the connector assembly. A ring electrode, carried by the distal end portion of the lead body, is disposed proximally of the second electrode in spaced-apart relationship thereto. The ring electrode is connected through a switching device to a node point along one or the other of the first and second conductors. The node point is located within the distal end portion of the lead body. The switching device has a first state permitting an electrical current to be conducted between the ring electrode and the node point and a second state in which the ring electrode is electrically isolated from the node point.

In a first illustrative embodiment, the tip electrode comprises a helical screw-in electrode extendable and retractable relative to the distal tip of the lead body. The helical screw-in electrode may have a proximal portion that is electrically insulated and a distal portion that is uninsulated.

Pursuant to one embodiment, the switching device may comprise a diode, preferably one that has a small form factor and a low forward voltage drop.

In another embodiment, the diode may have a cathode electrically connected to the node point and an anode electrically connected to the ring electrode, the node point being disposed along the first conductor. In yet another form of the invention, the diode may have an anode electrically connected to the node point and a cathode electrically connected to the ring electrode, the node point being disposed along the second conductor. In still a further form of the invention, the switching device may comprise back-to-back, oppositely poled diodes connected in parallel between the node point and the ring electrode, the node point being disposed along the second conductor.

According to another embodiment, the node point may be disposed along the second conductor, the second conductor including an electrical resistor disposed between the second electrode and the node point.

BRIEF DESCRIPTION OF THE DRAWINGS

The foregoing and other objects, features and advantages of the invention will be evident to those skilled in the art from the detailed description below, taken together with the accompanying drawings, in which.

DETAILED DESCRIPTION

The following description is not to be taken in a limiting sense but is made merely for the purpose of describing the general principles of the illustrated embodiments. The scope of the invention should be ascertained with reference to the issued claims. In the description that follows, like numerals or reference designators are used to refer to like parts or elements throughout.

Figure 1:
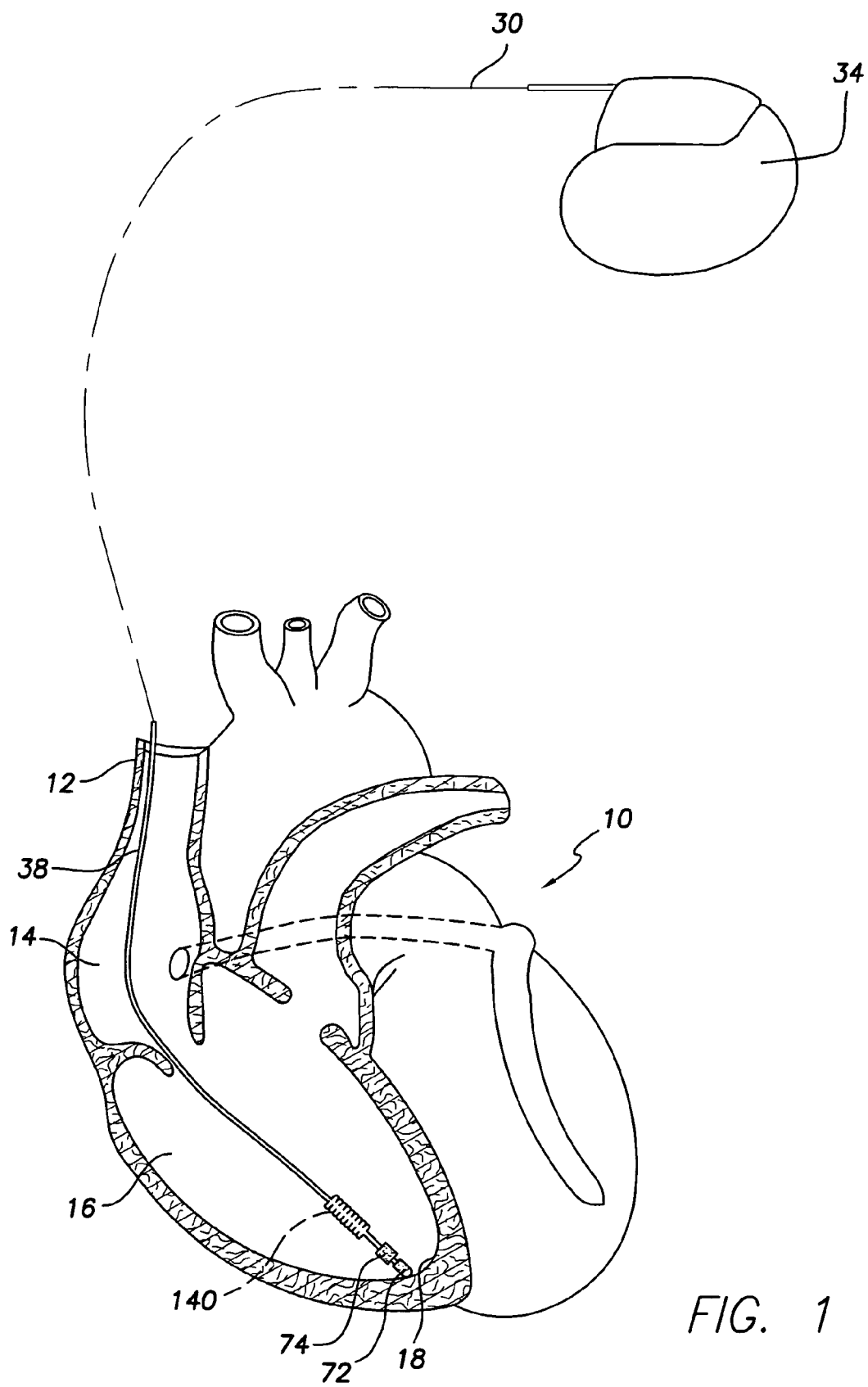
FIG. 1 is a perspective view of the anterior portion of a human heart showing two active fixation leads in accordance with the present invention, one of the leads being implanted within the right ventricle of the heart and the other lead being implanted in the coronary sinus region of the heart.

FIG. 1 depicts, in diagrammatic form, the anterior portion of a human heart 10, specifically showing the superior vena cava (SVC) 12; the right atrium (RA) 14; the right ventricle (RV) 16; and the apex 18 of the RV.

FIG. 1 shows, by way of example and not limitation, a bipolar, active fixation, pacing and sensing lead 30 in accordance with the invention placed within the RV 16. The lead 30 is electrically connected to an implantable medical device 34 which may comprise a pacemaker or a pacemaker combined with cardioverting and/or defibrillating functions. The lead 30 is shown by way of example only; it will be apparent that only a single lead or more than two leads may be utilized. For example, a second lead (not shown) may be placed within the right atrium 14 for stimulating and/or sensing the electrical activity of myocardial tissue lining that chamber. In addition, one or more leads may be placed within the veins in the coronary sinus region of the heart for left side pacing and/or sensing.

Figure 2:
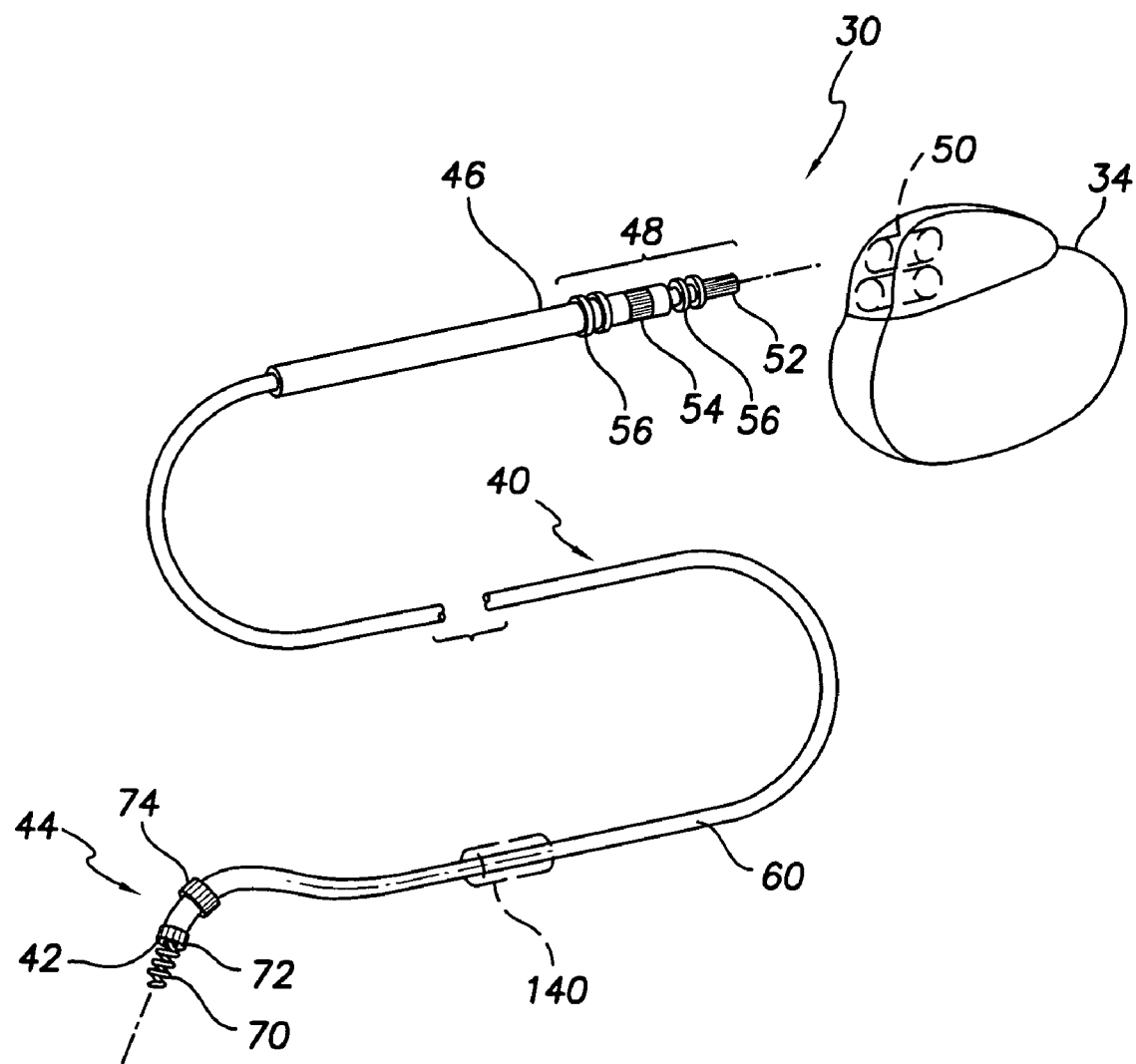
FIG. 2 is a perspective, exploded view of an implantable, transvenous, far-field rejecting cardiac pacing and sensing lead in accordance with one specific, exemplary embodiment of the invention.

FIG. 2 shows the lead 30 in greater detail. The lead 30 comprises a lead body 40 having a distal tip 42, a distal end portion 44 extending proximally from the distal tip 42, and a proximal end 46 carrying a conventional connector assembly 48 for electrically connecting the lead to the implantable medical device 34.

The connector assembly 48 carried by the proximal end of the lead body is adapted to electrically and mechanically couple the lead body 40 to the implantable medical device via a receptacle 50 that contains terminals connected to electronic circuitry enclosed within the medical device. For the embodiment under consideration, the connector assembly 48 includes two electrical contacts: a tubular contact pin 52 and a ring contact 54. The pin and ring contacts are positioned to engage corresponding electrical terminals within the receptacle 50. To prevent ingress of body fluids into the receptacle, the connector assembly may be provided with spaced-apart sets of seals 56. In accordance with well known implantation techniques, a stylet or guide wire (not shown) for delivering and steering the distal end portion of the lead body during placement thereof within the heart is inserted through the connector contact pin 52 and into a longitudinal passageway within the lead body 40, which passageway may comprise the lumen of a coil dedicated for that purpose or also serving as an electrical conductor connecting the contact pin with a helical, screw-in electrode to be described. Further, the electrical conductor may also function as an actuator for extending and retracting the helical electrode.

In well-known fashion, the lead body may comprise a tubular sheath or housing 60 made of an insulating, biocompatible, biostable material such as silicone rubber or polyurethane. By way of example and not limitation, the lead body 40 may be isodiametric with an outside diameter that may range from about 0.026 inch (2F) to about 0.104 inch (8F). In accordance with well-known techniques, the lead body 40 may have a lubricious coating to facilitate its movement through a heart delivery introducer and the patient's vascular system.

The distal end portion 44 of the lead body 40 carries three electrodes: a tip electrode preferably in the form of a helical screw-in electrode 70 extendable and retractable relative to the distal tip 42, a collar electrode 72 carried by the distal end portion 44 of the lead body at the distal tip thereof, and a ring electrode 74 carried by the distal end portion of the lead body and disposed proximally of the collar electrode 72. In accordance with one aspect of the present invention, the three electrodes are electrically connected to the connector assembly 48 by means only two electrical conductors.

Figure 3:
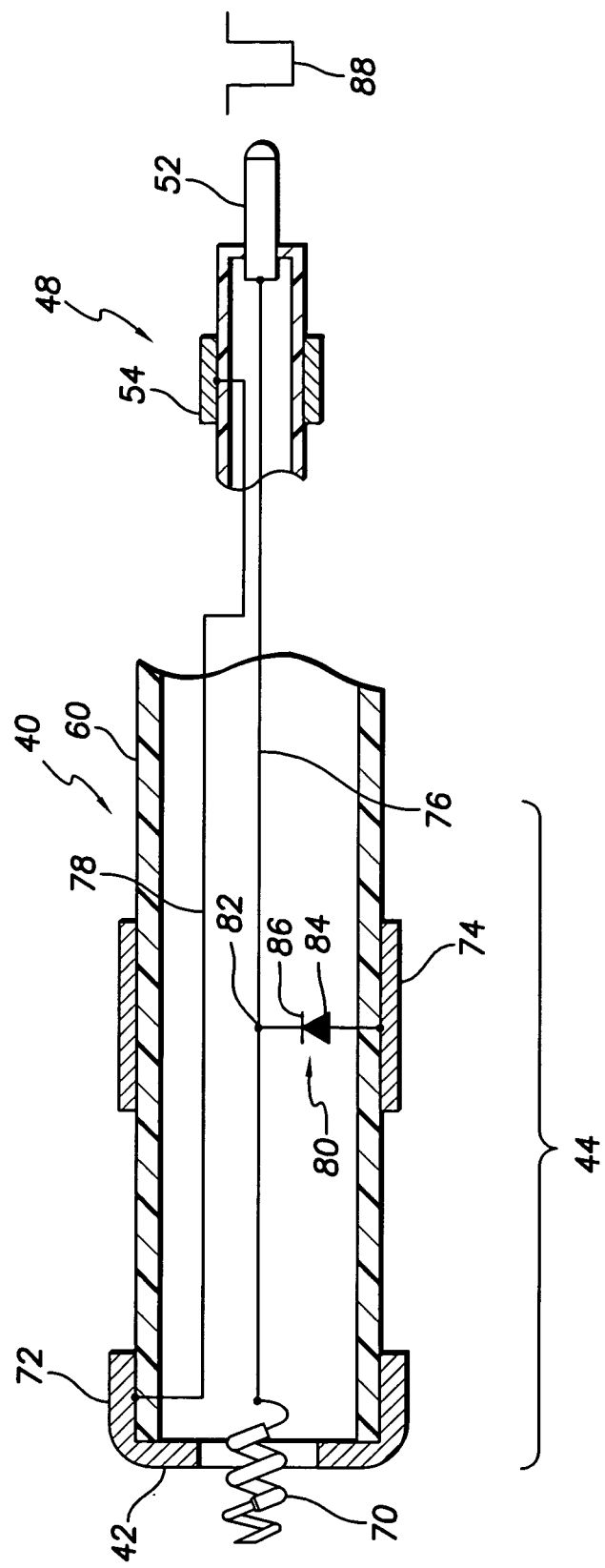
FIG. 3 is a schematic, side elevation view, in cross section, of a lead in accordance with the invention showing one way in which the electrodes of the lead may be electrically connected.

FIG. 3 illustrates the manner in which the electrodes 70, 72 and 74 may be connected in accordance with one specific, exemplary embodiment of the invention. Thus, the helical electrode 70 is electrically connected by a first electrical conductor 76 to a first electrical contact, preferably the pin contact 52, on the connector assembly 48 and the collar electrode 72 is electrically connected by a second electrical conductor 78 to a second electrical contact, preferably the ring contact 54, on the connector assembly 48. The ring electrode 74 is electrically connected through a switching device 80 to a node point 82 disposed along the first electrical conductor 76. The node point 82 is located within the distal end portion 44 of the lead body 40 so that only the two electrical conductors 76 and 78 extend the length of the lead body between the electrodes 70, 72 and 74 and the connector assembly 48. The switching device 80 has two states: a conducting state in which it permits electrical current to be conducted between the ring electrode 74 and the node point 82, and a non-conducting state in which the switching device 80 isolates the ring electrode 74 from the node point 82. In the embodiment of FIG. 3, the switching device 80 comprises a diode or rectifier appropriately poled to electrically separate or isolate a pacing dipole from a sensing dipole. By way of example, the diode 80 may comprise a Schottky diode such as a 1N5711 or the like characterized by a very low forward voltage drop (for example, 0.2V) and a very small form factor.

In the embodiment of FIG. 3, the anode 84 of the diode 80 is electrically connected to the ring electrode 74 while the diode's cathode 86 is electrically connected to the node point 82. Sensing is performed between the helical screw-in electrode 70 and the collar electrode 72. The small voltage, for example, 30 mV, generated by the heart is less than the forward drop (for example, 0.2V) of the diode which will therefore remain non-conducting. During pacing, the first electrical conductor 76 is pulsed negatively with respect to the collar (anode) electrode 72 by a voltage pulse 88 having a relatively large amplitude of, for example, 3V. This will pulse both the helical and ring electrodes 70 and 74 negatively, with the ring electrode potential being somewhat less, for example, 2.8V, resulting from the forward drop of the diode 80. The voltage at the ring 74, however, will be sufficient in the event the helical electrode 70 develops too high a pacing threshold because of scar tissue, for the ring to function as a backup cathode in a dipole comprising the collar and ring and electrodes 72 and 74, respectively.

Figure 4:
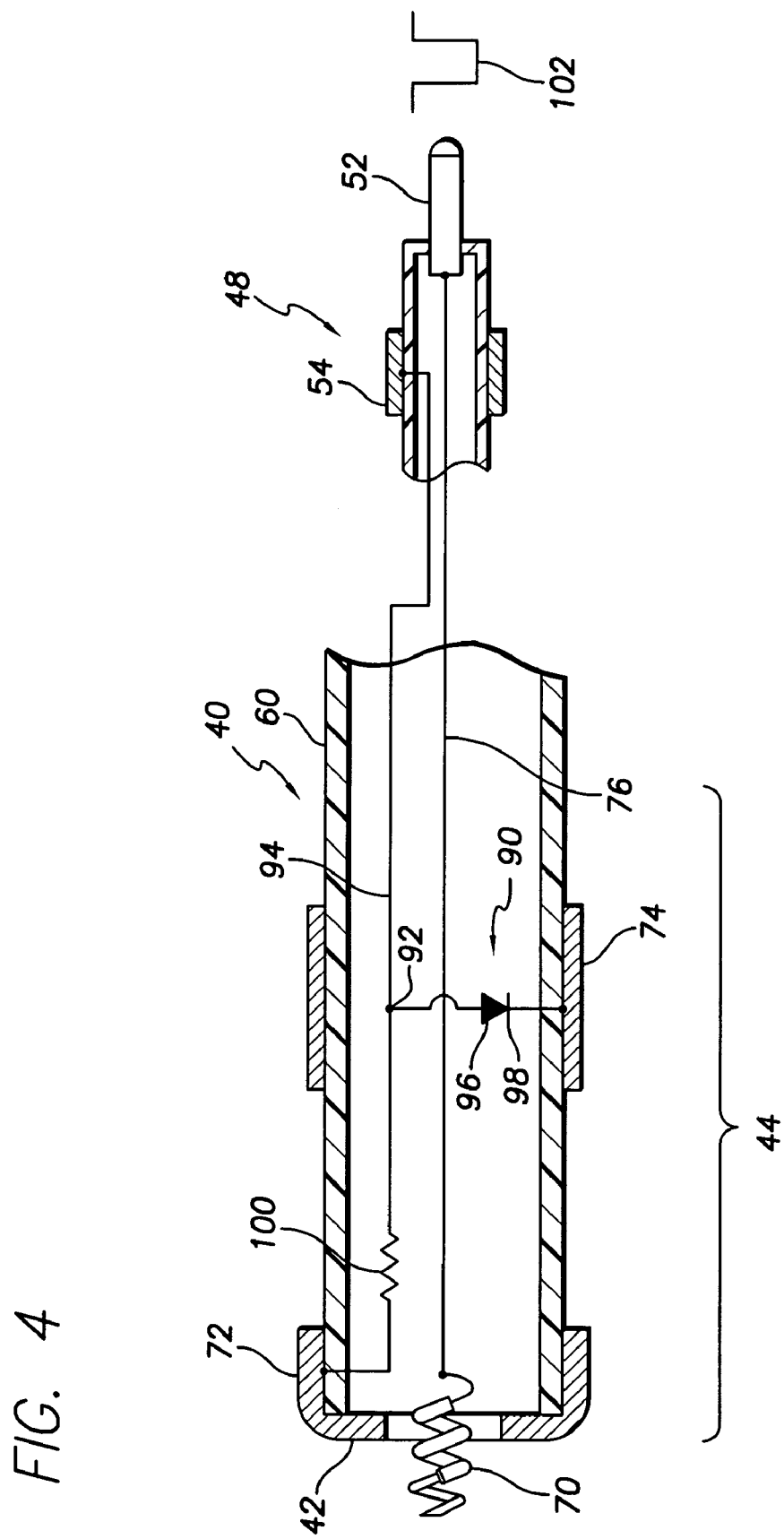
FIG. 4 is a schematic, side elevation view, in cross section, of a lead in accordance with the invention showing another way in which the electrodes of the lead may be electrically connected.

With reference to FIG. 4, in accordance with another specific, exemplary embodiment of the invention, there is incorporated within the distal end portion 44 of the lead body 40 a switching device 90 again preferably comprising a small form factor, low forward voltage drop diode such as a Schottky 1N5711, disposed between the ring electrode 74 and a node point 92, within the distal end portion 44 of the lead body, along a second electrical conductor 94 connecting the collar electrode 72 and the ring contact 54. The anode 96 of the diode 90 is electrically connected to the node point 92 while the diode's cathode 98 is electrically connected to the ring electrode 74. The second conductor 94 preferably incorporates a resistor 100 connected between the node point 92 and the collar electrode 72. In this embodiment, the helical screw-in electrode, connected to the pin contact 52 by the first electrical conductor 76, is completely isolated electrically from both the collar and the ring electrodes. As before, sensing is performed between the helical electrode 70 and the collar electrode 72. Pacing is performed between the helical electrode 70 and the ring electrode 74, such pacing being advantageous since it is known that helical electrode-to-ring electrode pacing provides very reliable long term thresholds. During pacing, a negative pacing pulse 102 is applied to the first conductor 76 and hence to the helical electrode 70. Return current will flow through the ring electrode 74, through the diode 90 and through the second conductor 94 back to the pulse generator. The presence of the resistor 100, whose value, by way of example, may be between 2,000 and 30,000 ohms, assures that no significant pacing current will be drawn through the collar electrode 72. However, the resistor will easily pass the sensing signal from the collar 72 and thus sensing will take place between the collar electrode and the helical electrode. In this case also, the diode 90 connected to the ring electrode 74 will block sensing level voltages.

Figure 5:
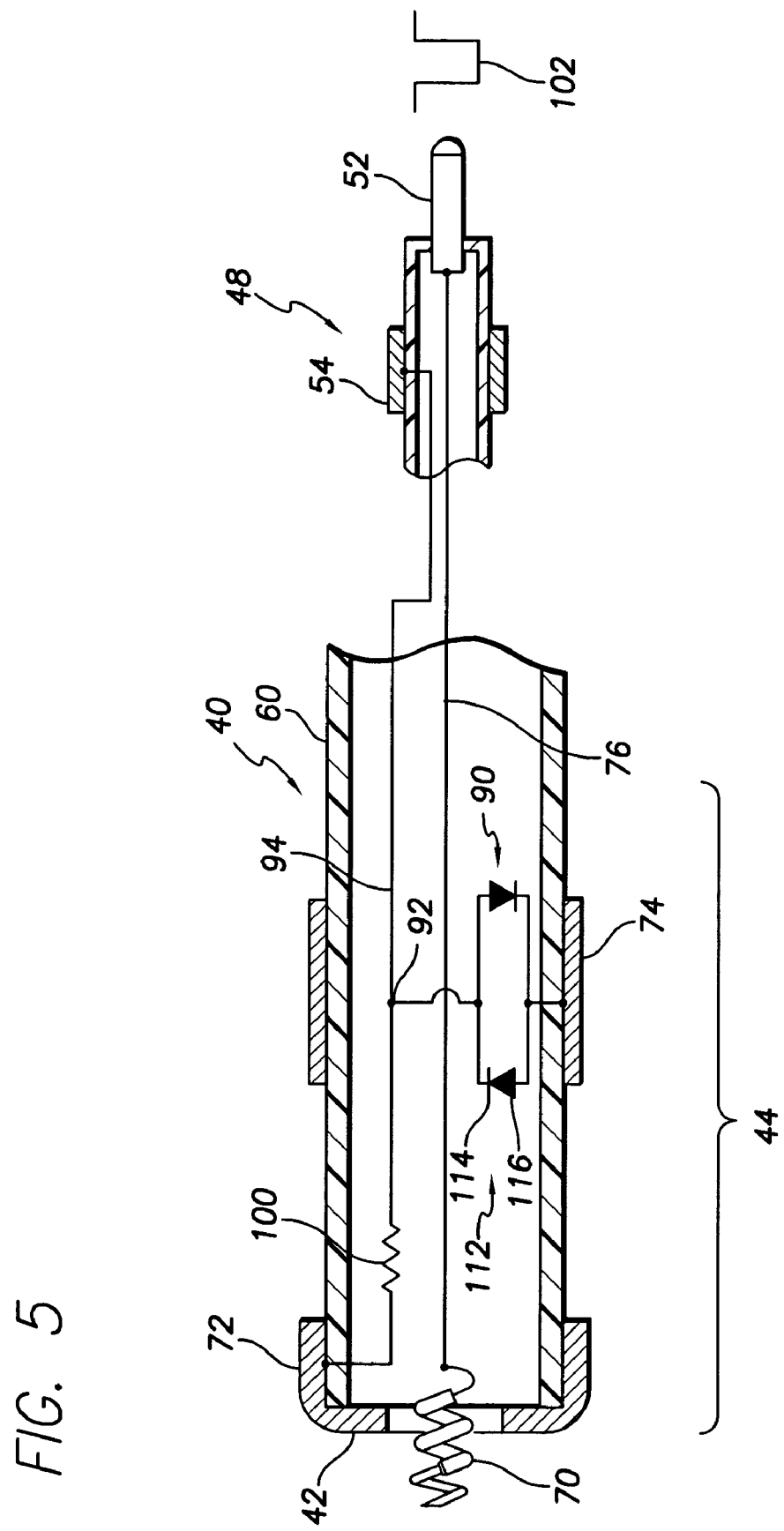
FIG. 5 is a schematic, side elevation view, in cross section, of a lead in accordance with the invention showing yet another way in which the electrodes of the lead may be electrically connected.

Yet another specific, exemplary embodiment of the invention is shown in FIG. 5. The embodiment of FIG. 5 is identical to that shown in FIG. 4 except that in the embodiment of FIG. 5 there is provided a switching device 110 comprising a pair of back-to-back, oppositely poled diodes 90 and 112 connected in parallel between the ring electrode 74 and the node point 92 along the second conductor 94. Like the diode 90, the diode 112 preferably comprises a small form factor, low forward voltage drop diode such as a Schottky 1N5711 diode. Like the embodiment of FIG. 4, the second conductor 94 preferably incorporates a resistor 100 having, for example, a resistance of between 2,000 and 30,000 ohms, between the node point 92 and the collar electrode 72. The operation of this embodiment is similar to that of the embodiment of FIG. 4 except that the additional diode 112 is poled so that its cathode 114 is connected to the node point 92 on the second conductor 94 and its anode 116 is connected to the ring electrode 74 will allow output capacitor recharge current to flow through the ring electrode. This arrangement minimizes DC corrosion-inducing current and polarization.

Figure 6:
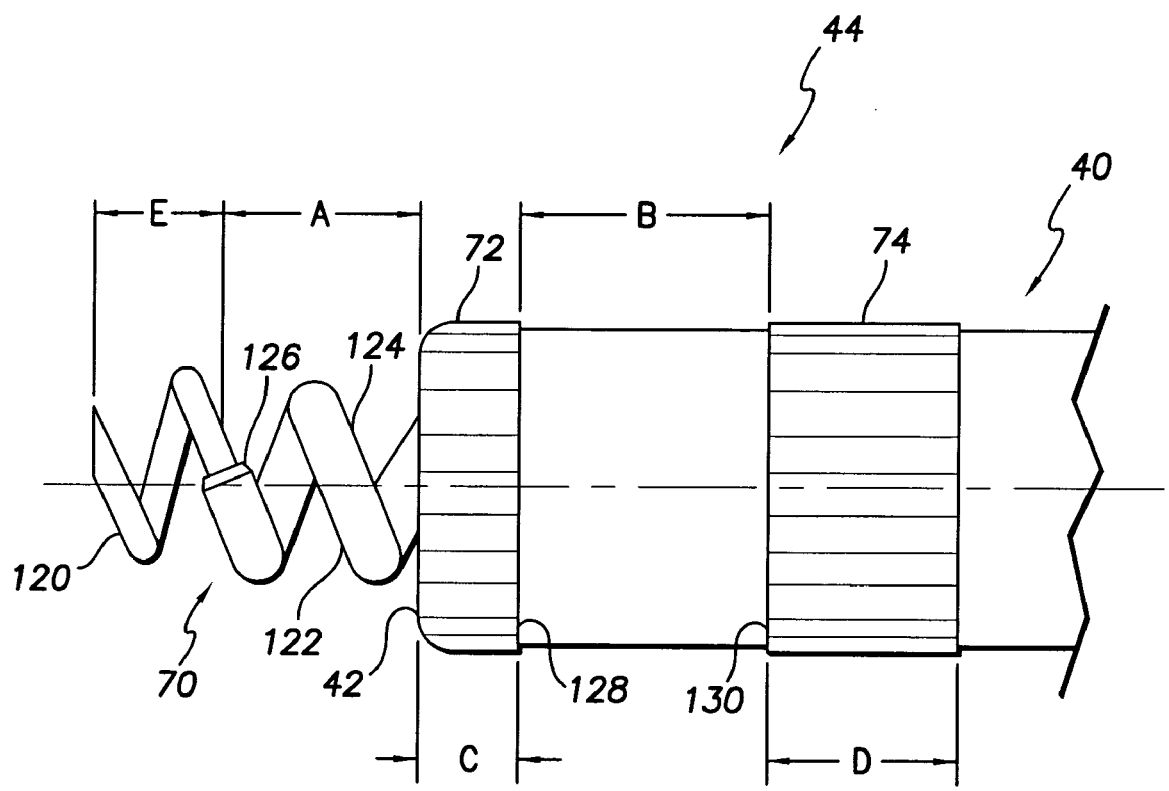
FIG. 6 is an enlarged side elevation view of the distal end portion of the lead shown in FIG. 2.

With reference to FIG. 6 showing an enlarged representation of the distal end portion 44 of the lead body 40, the helical, screw-in electrode 70 comprises an uninsulated or bare distal portion 120 projecting from a proximal portion 122 covered with an insulative coating 124 of parylene or the like. The insulative coating 124 has a distal edge 126 separated from the distal tip 42, that is, the distal extremity of the collar electrode 72, by an interelectrode spacing "A" when the helical electrode 70 is fully extended (as depicted in FIG. 6) relative to the distal tip 42 of the lead body. With the helical electrode 70 extended to anchor the distal end portion 44 of the lead body in the adjacent cardiac tissue, electrical contact will be established between the uninsulated distal portion 120 of the electrode 70 and the surrounding cardiac tissue. Further, the collar electrode 72 has a proximal edge 128 separated from a distal edge 130 of the ring electrode 74 by an interelectrode spacing "B".

The lead body 40 may be designed to optimize bipolar pacing and sensing with substantially complete far-field signal rejection. By way of example and not limitation, the uninsulated distal portion 120 of the helical electrode 70 may have a length, E, from 0.5 to 2.5 mm, and an electrically active surface area in the range of 3 to 12 $mm^2$. The collar electrode 72 may have an electrically active surface area in the range of 5 to 20 $mm^2$, and the anodal ring electrode 74 may have an electrically active surface area in the range of 10 to 40 $mm^2$. In the interest of maintaining low capture thresholds, the surface area of the ring electrode 74 may be preferably at least 15 $mm^2$. Further, by way of example, the interelectrode spacing "A" may be in the range of 0.3 to 1.5 mm to minimize the responsiveness of the helical electrode/collar electrode dipole to far-field potentials, while the interelectrode spacing "B" may be in the range of 5 to 30 mm. Still further by way of example, the length, C, of the collar electrode 72 may be in the range of 0.2 to 1.5 mm, while the length, D, of the ring electrode 74 may range from 0.5 to 30 mm.

The foregoing electrode parameters tend to optimize the pacing and sensing performance of the lead by providing clinically acceptable P-wave signal amplitudes while significantly attenuating R-wave far-field signals and mitigating T-wave oversensing without compromising pacing thresholds or device features such as autocapture and morphology discrimination. Further, where a cardioverting/defibrillating electrode is included, the electrode parameters of the present invention permit it to be positioned closer to the ring electrode 74 and thereby closer to the distal tip 42 of the lead body.

In conventional fashion, and by way of example and not limitation, the electrodes 70, 72 and 74 may be formed of a base material comprising a platinum-iridium alloy or titanium having a surface coating that may comprise titanium nitride, platinum oxide, iridium, or iridium oxide. The collar and ring electrodes may have any lengths compatible with maintaining the flexibility of the distal end of the lead body. The interelectrode spacings between the electrodes are preferably such as to be compatible with or to optimize the pacing and sensing in either the right atrium or right ventricle. The determination of such spacings will typically depend upon such factors as the particular site selected to receive the distal end of the lead, the patient's anatomy, and so forth.

The distal end portion 44 of the lead body may also carry a cardioverting/defibrillating shocking electrode 140 (FIGS. 1 and 2) proximal of the ring electrode 74. The shocking electrode 140 may comprise a conventional, elongated electrically conductive coil wound around the outside surface of the lead body housing 60. Alternatively, the shocking electrode may be fabricated of a conductive polymer. For greater flexibility, the shocking electrode may comprise a series of spaced-apart, relatively short rings of metal or of a conductive polymer. In any event, each shocking electrode is electrically coupled to a separate contact on the connector assembly 48, in well-known fashion.

The insulating, tubular housing 60 encloses the electrical conductors 76, 78 and 94 which may be fabricated of MP35N or MP35N/Ag alloy or the like connecting the electrodes along the distal end portion of the lead body with the terminal contacts on the connector assembly 48. Preferably, the housing 60 comprises a multilumen structure and the conductors preferably comprise multifilar coils or braided cables, although a coil conductor in combination with a cable conductor may also be used.

The distal end portion 44 of the lead body may also comprise fixation means in the place of the fixation provided by the helical screw-in electrode. For example, the distal end portion 44 may be configured to stabilize the distal end portion within a target site within the heart, for example, the myocardium within the right ventricle or a coronary vessel of the coronary sinus region. In this connection, for implantation within a coronary vessel, the distal end portion 44 of the lead body 40 may include passive fixation or anchoring means (not shown) comprising, for example, one or more preformed projections, humps, helices, spirals, S-shaped bends or other structural elements or features manufactured into the distal end portion of the lead body designed to provide biased contact between the distal end of the lead body and the inner wall of the target vessel so as to create frictional forces sufficient to wedge or stabilize the distal end and prevent its displacement or dislodgement. The passive fixation means may also include texturization (not shown) of at least a portion of the distal end portion of the lead body to promote rapid blood clotting and resulting fibrotic growth to further help stabilize or anchor the distal end of the lead body. For left side placement, instead of a helical electrode, there may be provided at the distal tip of the lead body a tip electrode that may comprise, for example, a non-extendable/retractable electrode in the form of an annular ring, a hemispherical dome electrode, or other geometrically configured electrode compatible with the coronary venous anatomy.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. A cardiac lead for transmitting electrical pacing and sensing signals between an electrical medical device and selected cardiac tissue, the lead comprising:
   a lead body having a proximal end, a distal tip and a distal end portion extending proximally from the distal tip, the proximal end of the lead body carrying a connector assembly electrically connectable to the electrical medical device;
   a first pacing/sensing electrode at the distal tip of the lead body;
   a first electrical conductor within the lead body electrically connecting the first pacing/sensing electrode to a first electrical contact on the connector assembly;
   a second pacing/sensing electrode carried by the distal end portion of the lead body at the distal tip thereof;
   a second electrical conductor within the lead body electrically connecting the second electrode to a second electrical contact on the connector assembly; and
   a third pacing/sensing electrode carried by the distal end portion of the lead body, the third electrode being disposed proximally of the second pacing/sensing electrode in spaced-apart relationship thereto, a switching device connecting the third pacing/sensing electrode to a node point along the first electrical conductor to electrically separate a pacing dipole from a sensing dipole;

wherein during pacing, the switching device has a first state permitting an electrical current to be conducted between the third pacing/sensing electrode and the node point when the first electrical conductor is pulsed with a sufficient voltage pulse amplitude to pulse both the first pacing/sensing electrode and the third pacing/sensing electrode such that the third pacing/sensing electrode is a backup electrode in a dipole comprising the second pacing/sensing electrode and the third pacing/sensing electrode when the first pacing/sensing electrode develops too high a pacing threshold; and wherein during sensing, the switching device has a second state in which the third pacing/sensing electrode is electrically isolated from the node point when voltage generated by the heart is insufficient to switch the switching device from a non-conducting state to a conducting state such that sensing is performed between the first pacing/sensing electrode and the third pacing/sensing electrode.

2. The lead of claim 1 in which:
the switching device comprises a diode.

3. The lead of claim 2 in which:
the diode comprises a cathode electrically connected to the node point and an anode electrically connected to the third pacing/sensing electrode, the node point being disposed along the first conductor.

4. The lead of claim 1 in which:
the lead body carries a shocking electrode positioned proximally of the third pacing/sensing electrode, the shocking electrode being adapted to be electrically connected to a separate contact on the connector assembly.

5. The lead of claim 1 in which:
the first pacing/sensing electrode and the second pacing/sensing electrode comprise a sensing dipole.

6. The lead of claim 1 in which:
the first pacing/sensing electrode and the second pacing/sensing electrode comprise a pacing dipole.

7. The lead of claim 1 in which:
the second pacing/sensing electrode and the third pacing/sensing electrode comprise a pacing dipole.

8. A cardiac lead for transmitting electrical pacing and sensing signals between an electrical medical device and selected cardiac tissue, the lead comprising:
a lead body having a proximal end, a distal tip and a distal end portion extending proximally from the distal tip, the proximal end of the lead body carrying a connector assembly electrically connectable to the electrical medical device;
a helical screw-in pacing/sensing electrode extendable and retractable relative to the distal tip of the lead body;
a first electrical conductor within the lead body electrically connecting the helical screw-in pacing/sensing electrode to a first electrical contact on the connector assembly;
a collar pacing/sensing electrode carried by the distal end portion of the lead body at the distal tip thereof;
a second electrical conductor within the lead body electrically connecting the collar pacing/sensing electrode to a second electrical contact on the connector assembly; and
a ring pacing/sensing electrode carried by the distal end portion of the lead body, the ring pacing/sensing electrode being disposed proximally of the collar pacing/sensing electrode in spaced-apart relationship thereto, the ring pacing/sensing electrode being connected through a switching device to a node point along the first electrical conductor to electrically separate a pacing dipole from a sensing dipole;

wherein during pacing, the switching device has a first state permitting an electrical current to be conducted between the ring pacing/sensing electrode and the node point when the first electrical conductor is pulsed with a sufficient voltage pulse amplitude to pulse both the helical screw-in pacing/sensing electrode and the ring pacing/sensing electrode such that the ring pacing/sensing electrode is a backup electrode in a dipole comprising the collar pacing/sensing electrode and the ring pacing/sensing electrode when the helical screw-in pacing/sensing electrode develops too high a pacing threshold; and wherein during sensing, the switching device has a second state in which the ring pacing/sensing electrode is electrically isolated from the node point when voltage generated by the heart is insufficient to switch the switching device from a non-conducting state to a conducting state such that sensing is performed between the helical screw-in pacing/sensing electrode and the collar pacing/sensing electrode.

9. The lead of claim 8 in which:
the helical screw-in pacing/sensing electrode and the collar pacing/sensing electrode comprise a sensing dipole.

10. The lead of claim 8 in which:
the helical screw-in pacing/sensing electrode and the collar pacing/sensing electrode comprise a pacing dipole.

11. The lead of claim 8 in which:
the collar pacing/sensing electrode and the ring pacing/sensing electrode comprise a pacing dipole.

12. The lead of claim 8 in which:
the switching device comprises a diode and the diode remains nonconducting when a voltage generated by the heart is less than a forward voltage drop of the diode.

13. The lead of claim 8 in which:
the interelectrode spacing between a distal extremity of the ring pacing/sensing electrode and a proximal extremity of the collar pacing/sensing electrode ranges from 5 to 30 mm.

* * * * *